(12) United States Patent
Sun et al.

(10) Patent No.: US 11,040,933 B2
(45) Date of Patent: Jun. 22, 2021

(54) PREPARATION METHOD OF PHENOXYCARBOXYLIC ACID HERBICIDES

(71) Applicant: SHANDONG RAINBOW BIOTECH CO., LTD., Shandong (CN)

(72) Inventors: Guoqing Sun, Shandong (CN); Yongsheng Hou, Shandong (CN); Liguo Zhang, Shandong (CN); Zhilong Chi, Shandong (CN); Yishan Hu, Shandong (CN)

(73) Assignee: SHANDONG RAINBOW BIOTECH CO., LTD., Shandong (CN)

( * ) Notice: Subject to any disclaimer, the term of this patent is extended or adjusted under 35 U.S.C. 154(b) by 0 days.

(21) Appl. No.: 16/980,441

(22) PCT Filed: Feb. 18, 2019

(86) PCT No.: PCT/CN2019/075321
§ 371 (c)(1),
(2) Date: Sep. 14, 2020

(87) PCT Pub. No.: WO2019/179267
PCT Pub. Date: Sep. 26, 2019

(65) Prior Publication Data
US 2021/0017113 A1   Jan. 21, 2021

(30) Foreign Application Priority Data
Mar. 19, 2018  (CN) .......................... 201810226589.5

(51) Int. Cl.
*C07C 51/09*   (2006.01)
*C07C 51/47*   (2006.01)
(Continued)

(52) U.S. Cl.
CPC .............. *C07C 51/09* (2013.01); *A01N 37/10* (2013.01); *C07C 51/47* (2013.01); *C07C 67/307* (2013.01); *C07C 67/31* (2013.01); *C07C 2601/16* (2017.05)

(58) Field of Classification Search
None
See application file for complete search history.

(56) References Cited

U.S. PATENT DOCUMENTS 4,326,882 A   4/1982 Richter et al.

FOREIGN PATENT DOCUMENTS

CN   106242971 A   12/2016
CN   106278862 A   1/2017
(Continued)

OTHER PUBLICATIONS

International Search Report for PCT/CN2019/075321 dated May 13, 2019, ISA/CN.
Sun, Changjun et al., Synthesis of 2,4-dichlorophenol by selective chlorination. Henan Chemical Industry, No. 11, Nov. 27, 1990(Nov. 27, 1990), ISSN:1003-3467, p. 19, lines 3-7.
(Continued)

*Primary Examiner* — Amy C Bonaparte
(74) *Attorney, Agent, or Firm* — Yue (Robert) Xu; Apex Attorneys at Law, LLP

(57) ABSTRACT

Disclosed is a preparation method of phenoxycarboxylic acid herbicides. The preparation method comprises the following steps. S1: mixing an anhydrous phenol and a basic substance with a chloro-substituted carboxylic acid ester and performing a one-pot condensation reaction in an anhydrous system to obtain a phenoxycarboxylic acid ester. The chloro-substituted carboxylic acid ester is represented by the formula $ClR_1COOR$, in which $R_1$ is a C1-3 alkanediyl or alkylidene group, R is a C1-10 alkyl group or a C3-10 cycloalkyl group; S2: the phenoxycarboxylic acid ester undergoes selective chlorination with a chlorinating agent in (Continued)

the presence of a first catalyst and a second catalyst to obtain a chloro-substituted phenoxycarboxylic acid ester; and S3: the chloro-substituted phenoxycarboxylic acid ester undergoes an acid hydrolysis reaction to obtain a phenoxycarboxylic acid herbicide represented by formula I, in which $R_3$ is H, Cl or $CH_3$.

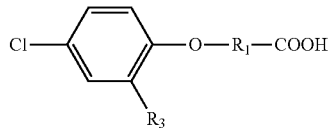

(I)

(51) Int. Cl.
*C07C 67/31* (2006.01)
*C07C 67/307* (2006.01)
*A01N 37/10* (2006.01)

(56) References Cited

FOREIGN PATENT DOCUMENTS

| CN | 106892808 | * | 6/2017 |
| CN | 106892808 A | | 6/2017 |
| CN | 108424360 | * | 8/2018 |
| CN | 108947794 A | | 12/2018 |
| CN | 108947822 A | | 12/2018 |
| CN | 108947838 A | | 12/2018 |

10 Claims, 2 Drawing Sheets

* cited by examiner

PREPARATION METHOD OF PHENOXYCARBOXYLIC ACID HERBICIDES

CROSS REFERENCE TO RELATED APPLICATIONS

This application is the national phase of International Application No. PCT/CN2019/075321, titled "PREPARATION METHOD OF PHENOXYCARBOXYLIC ACID HERBICIDES", filed on Feb. 18, 2019, which claims the priority of Chinese Patent Application No. 201810226589.5, filed on Mar. 19, 2018, filed with China National Intellectual Property Administration, and titled with "PREPARATION METHOD OF PHENOXYCARBOXYLIC ACID HERBICIDES", and the disclosures of which are hereby incorporated by reference.

FIELD

The present disclosure relates to the technical field of organic synthesis, specifically to a method for preparing a phenoxycarboxylic acid herbicide.

BACKGROUND

Phenoxycarboxylic acid herbicides are an important type of herbicides. They are widely used in agriculture due to their high herbicidal speed and wide herbicidal spectrum. The necessary conditions for the structure of the phenoxycarboxylic acid active compound include: a benzene ring, an oxygen atom substitution on the ring; an aliphatic chain and a carboxyl group connected to the oxygen atom; and different substituents on the benzene ring, wherein the compound substituted at the $2^{nd}$ and $4^{th}$ positions has the highest activity. Different herbicide species can be formed due to structural differences of groups such as benzene ring substituents; acids and esters of such herbicides are more used in agricultural production. Such herbicides include phenoxycarboxylic acid compounds having the following structural formula:

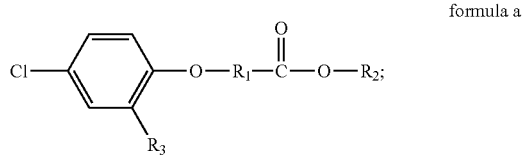

formula a in formula a, $R_1$ is an alkylene or an alkylidene group with 1~3 carbon atoms, $R_2$ is H, an alkyl or a cycloalkyl group with 3~10 carbon atoms, and $R_3$ is H, Cl or $CH_3$.

A commonly used method for preparing the above-mentioned phenoxycarboxylic acid herbicide ($R_2$ is H) mainly has the following two steps: (1) performing a chlorination of phenol, which is used as main raw material, to obtain a chlorophenol; (2) performing a condensation reaction of the chlorophenol with a chlorinated carboxylic acid under alkaline conditions, and acidizing and filtrating the obtained reaction solution to obtain an acid in a phenoxycarboxylic acid herbicide wet material, which is dried to obtain a phenoxycarboxylic acid herbicide.

Among the above methods, the chlorophenol produced in the step (1) has an extremely unpleasant pungent odor, resulting in a very poor environment at the production site and poor chlorination selectivity. In step (2), dichlorophenol or polychlorophenol in the chlorophenol will undergo condensation reaction between the two molecules, resulting in a highly toxic substance, dioxin, which produces a large amount of hazardous waste of chlorophenol and chlorophenoxy carboxylic acid, and produces a large amount of wastewater containing hydroxyl carboxylic acid and waste salt. The three wastes involve high treatment pressure and high processing costs. The prepared phenoxycarboxylic acid herbicide product also contains dioxin, which poses great risks to the health of the environment and production personnel, and results in poor quality of the products. In addition, dioxin will enter the plant, air, soil and water sources with the use of phenoxycarboxylic acid herbicides and their derivatives, and will result in more serious environmental and health hazards as the food chain is enriched.

SUMMARY

In view of this, the technical problem to be solved by the present disclosure aims to provide a method for preparing a phenoxycarboxylic acid herbicide, which can improve the product quality and the operating environment at the production site, and reduce the output of three wastes.

The present disclosure provides a method for preparing a phenoxycarboxylic acid herbicide, comprising the following steps of:

S1, mixing an anhydrous phenolic compound, an alkaline substance and a chlorocarboxylic ester, and performing a one-pot condensation reaction in a non-aqueous system to obtain a phenoxycarboxylic ester; the anhydrous phenolic compound is anhydrous phenol or anhydrous o-cresol;

the general formula of the chlorocarboxylic ester is $ClR_1COOR$, wherein $R_1$ is selected from an alkylene or an alkylidene group with 1~3 carbon atoms, R is selected from an alkyl group with 1~10 carbon atoms or a cycloalkyl group with 3~10 carbon atoms;

S2, performing a selective chlorination of the phenoxycarboxylic ester with a chlorinating agent in the presence of a first catalyst and a second catalyst to obtain a chlorophenoxy carboxylic ester; the first catalyst is selected from a Lewis acid, and the second catalyst is selected from a thioether compound with 5~22 carbon atoms, a thiazole compound with 5~22 carbon atoms, an isothizaole compound with 5~22 carbon atoms, or a thiophene compound with 5~22 carbon atoms;

S3, performing an acidolysis reaction of the chlorophenoxy carboxylic ester to obtain the phenoxycarboxylic acid herbicide represented by formula I;

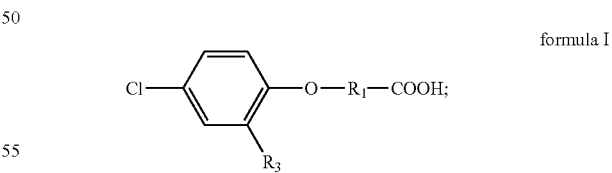

formula I in formula I, $R_1$ is selected from an alkylene or an alkylidene group with 1~3 carbon atoms, and $R_3$ is H, Cl or $CH_3$.

Preferably, in step S1, the alkaline substance is lithium carbonate, sodium carbonate, potassium carbonate or cesium carbonate.

Preferably, in step S1, the molar ratio of the anhydrous phenolic compound to the alkaline substance is 1:(1~1.08), and the molar ratio of the anhydrous phenolic compound and the chlorocarboxylic ester is 1:(1~1.08).

Preferably, in step S1, the temperature of the condensation reaction is 60~120° C.

Preferably, the step S1 specifically is: mixing the anhydrous phenolic compound, the alkaline substance and the chlorocarboxylic ester, then heating the mixture and keeping the temperature constant to react for 2 h~5 h to obtain a liquid containing condensation product, and filtering and drying to obtain a phenoxycarboxylic ester.

Preferably, in step S2, the chlorinating agent is chlorine gas, thionyl chloride or sulfuryl chloride.

Preferably, in step S2, the molar ratio of the phenoxycarboxylic ester to the chlorinating agent is 1:(1.98~2.4), and in step S3 R3 is Cl;

or alternatively, the molar ratio of the phenoxycarboxylic ester to the chlorinating agent is 1:(0.99~1.2), and in step S3 $R_3$ is H or $CH_3$.

Preferably, in step S2, the first catalyst is used in an amount of 0.05%~1.0% by weight based on the phenoxycarboxylic ester, and the second catalyst is used in an amount of 0.05%~1.0% by weight based on the phenoxycarboxylic ester.

Preferably, in step S2, the temperature of the selective chlorination is −20~100° C.

Preferably, in step S3, the acid used for acidolysis is substances of hydrochloric acids, phosphoric acids, sulfuric acids or sulfonic acids.

The present disclosure performs a condensation reaction of phenol to synthesize phenoxycarboxylic ester, and then performs a selective chlorination to synthesize chlorophenoxy carboxylic ester, and finally acidifies to synthesize phenoxycarboxylic acid herbicide. Compared with the existing synthetic technology, the present disclosure effectively avoids the production and use of chlorophenol with unpleasant odor, fundamentally eliminates the production of highly toxic dioxins, and greatly improves product quality and operating environment at the production site. In the present disclosure, a one-pot condensation reaction of a phenolic compound, an alkaline and a chlorocarboxylic ester in a non-aqueous system not only does not produce waste water containing a hydroxycarboxylic acid and a metal chloride, and does not require the use of a solvent, and the entire production process will not produce hazardous waste containing chlorophenol and chlorophenoxy carboxylic acid, which greatly reduces the amount of three waste treatment, the treatment difficulty of three waste, treatment cost and energy consumption. Experiments show that the content of the obtained phenoxycarboxylic acid herbicide product is ≥98.5%, and the total yield is ≥98%. The present disclosure adopts phenolic compound as a raw material, obtains highquality phenoxycarboxylic acid herbicide by condensation reaction, selective chlorination and acidolysis, and the method of the present disclosure effectively avoids loss of active ingredients and improves product yield. In addition, the present disclosure effectively eliminates the production of high COD and high-salt wastewater by the innovation of the process route, and the output of waste salt (metal chloride) has been reduced by more than 50%, the output of three wastes has been greatly reduced, and the treatment cost of three wastes has dropped significantly.

DETAILED DESCRIPTION

Figure 1:
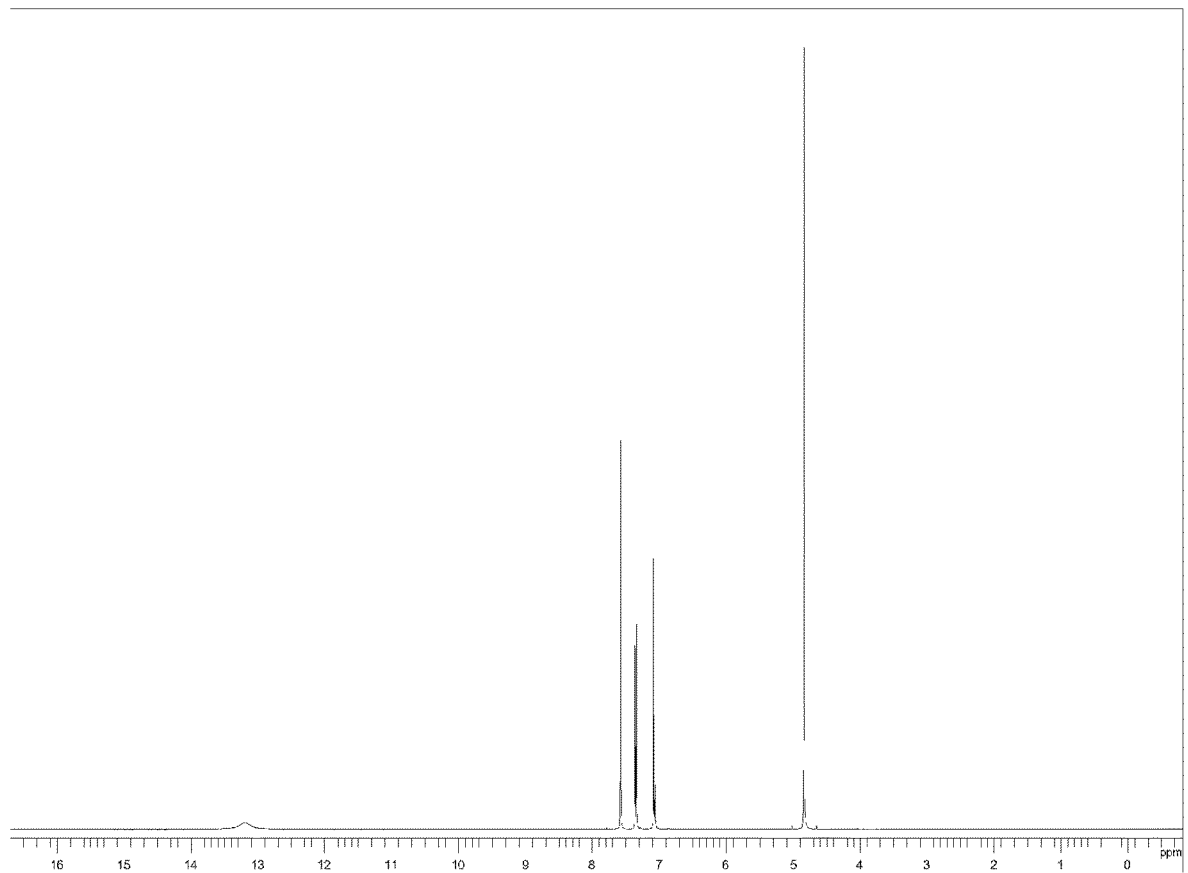
FIG. 1 is a nuclear magnetic resonance spectrum of 2,4-dichlorophenoxyacetic acid obtained in Example 1 of the present disclosure.

The present disclosure provides a method for preparing a phenoxycarboxylic acid herbicide, comprising the following steps of:

S1, mixing an anhydrous phenolic compound, an alkaline substance and a chlorocarboxylic ester, and performing a one-pot condensation reaction in a non-aqueous system to obtain a phenoxycarboxylic ester; the anhydrous phenolic compound is anhydrous phenol or anhydrous o-cresol;

the general formula of the chlorocarboxylic ester is $ClR_1COOR$, wherein $R_1$ is selected from an alkylene or an alkylidene group with 1~3 carbon atoms, R is selected from an alkyl group with 1~10 carbon atoms or a cycloalkyl group with 3~10 carbon atoms;

S2, performing a selective chlorination of the phenoxycarboxylic ester with a chlorinating agent in the presence of a first catalyst and a second catalyst to obtain a chlorophenoxy carboxylic ester; the first catalyst is selected from a Lewis acid, and the second catalyst is selected from a thioether compound with 5~22 carbon atoms, a thiazole compound with 5~22 carbon atoms, an isothizaole compound with 5~22 carbon atoms, or a thiophene compound with 5~22 carbon atoms;

S3, performing an acidolysis reaction of the chlorophenoxy carboxylic ester to obtain the phenoxycarboxylic acid herbicide represented by formula I;

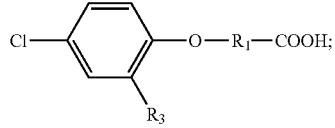

formula I in formula I, $R_1$ is selected from an alkylene or an alkylidene group with 1~3 carbon atoms, and $R_3$ is H, Cl or $CH_3$.

The method for preparing the phenoxycarboxylic acid herbicide provided by the present disclosure can improve the operating environment at the production site, and has the advantages of good product quality, high yield, and less three wastes.

In embodiments of the present disclosure, a phenolic compound is used as a main raw material, a certain proportion of an alkaline substance and a chlorocarboxylic ester are added at a certain temperature to react to obtain a phenoxycarboxylic ester. Wherein, the phenolic compound according to the present disclosure refers to phenol or o-cresol.

The general formula of the chlorocarboxylic ester is $ClR_1COOR$, wherein $R_1$ is selected from an alkylene or an alkylidene group with 1~3 carbon atoms, specifically, $R_1$=$CH_2$, $CH(CH_3)$ or $(CH_2)_3$. R is selected from an alkyl group with 1~10 carbon atoms or a cycloalkyl group with 3~10 carbon atoms, preferably an alkyl group with 1~4 carbon atoms. In an embodiment of the present disclosure, the chlorocarboxylic ester is methyl chloroacetate, ethyl chloroacetate, isopropyl chloroacetate, n-butyl chloroacetate, isobutyl chloroacetate, isooctyl chloroacetate, nbutyl chloropropionate, n-decyl chloropropionate, ethyl chlorobutyrate or isooctyl chlorobutyrate.

The present disclosure performs a condensation reaction of the above phenolic compound and a chlorocarboxylic ester ClR₁COOR to form a phenoxycarboxylic ester, and the phenoxycarboxylic ester refers to a substance having the following structure:

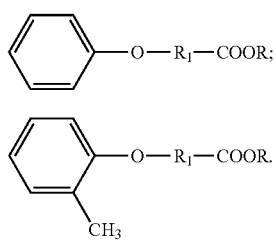

formula II-1 formula II-2

The present disclosure performs a condensation reaction in the presence of an alkaline substance to obtain chlorides and phenoxycarboxylic ester; the alkaline substance is preferably lithium carbonate, sodium carbonate, potassium carbonate or cesium carbonate. In the present disclosure, the molar ratio of the phenolic compound to the chlorocarboxylic ester may be 1:(1~1.08), preferably 1:(1~1.04), and more preferably 1:(1.02~1.04). The temperature of the condensation reaction may be 60~120° C., preferably 60~100° C., and more preferably 80~100° C. The resulting liquid containing condensation product is filtered, and conventionally dried to obtain a crude product; wherein the filtration temperature generally is 30~50° C.

In an embodiment of the present disclosure, the condensation reaction is carried out in the absence of a solvent. Specifically, in the embodiment of the present disclosure, a certain proportion of anhydrous phenolic compound, alkali and chlorocarboxylic ester are put into the reactor together, and the temperature is raised to a certain temperature, preferably the mixture is kept constant in the temperature to react for 2 h~5 h to obtain a liquid containing condensation product, which is filtered and dried to obtain a phenoxycarboxylic ester.

Wherein, the alkaline refers to lithium carbonate, sodium carbonate, potassium carbonate or cesium carbonate. The anhydrous phenolic compound according to the present disclosure refers to anhydrous phenol or anhydrous o-cresol, and the anhydrous phenolic compound according to the present disclosure refers to the phenol or o-cresol having a water content of ≤0.1%; and the molar ratio of the phenolic compound to the alkaline is 1:(1~1.08), preferably 1:(1~1.04), and more preferably 1:(1.02~1.04). The molar ratio of the phenolic compound to the chlorocarboxylic ester may be 1:(1~1.08), preferably 1:(1~1.04), and more preferably 1:(1.02~1.04). The temperature of the condensation reaction may be 60~120° C., preferably 60~100° C., and more preferably 80~100° C.

In the method according to the present disclosure, a one-pot condensation reaction of a phenolic compound, an alkaline and a chlorocarboxylic ester in a non-aqueous system not only does not produce waste water containing hydroxycarboxylic acid and metal chlorides, and does not require the use of a solvent, and the entire production process will not produce hazardous waste containing chlorophenol and chlorophenoxy carboxylic acid, which greatly reduces the amount of three waste treatment, the treatment difficulty of three waste, treatment cost and energy consumption.

After obtaining the phenoxycarboxylic ester, in the embodiment of the present disclosure, a certain proportion of the first catalyst and the second catalyst are added thereto, then, a certain amount of chlorinating agent is added at a certain temperature to carry out selective chlorination, and after the addition is completed the mixture is kept constant in the temperature to react for 0.5 h to obtain chlorophenoxy carboxylic ester.

In the present disclosure, the first catalyst is Lewis acid. A substance that generally accepts one electron pair is Lewis acid; the Lewis acid catalyst of the present disclosure generally comprises: (1) a chloride containing Mg, Fe, Al, Zn, Ti or Sn; (2) an oxide containing Mg, Fe, Al, Zn, Ti or Sn; (3) a fluoride such as BF3, SbF5; (4) acetic acid compounds such as Pb(OAc)₂, Zn(OAc)₂. Specifically, the first catalyst comprises but is not limited to SnCl₄, MgCl₂, FeCl₃, AlCl₃, ZnCl₂, TiCl₄, BF₃, SbF₅, Al₂O₃, Fe₂O₃, TiO₂, Pb(OAc)₂, Zn(OAc)₂ or Al₂O(OAc)₄, preferably MgCl₂, FeCl₃, ZnCl₂, SbF₅, TiO₂, Pb(OAc)₂, and more preferably FeCl₃, TiO₂, Pb(OAc)₂.

In the present disclosure, the second catalyst is a thioether compound with 5~22 carbon atoms, a thiazole compound with 5~22 carbon atoms, an isothiazole compound with 5~22 carbon atoms, or a thiophene compound with 5~22 carbon atoms, preferably a thioether, a thiazole, a isothiazole, a thiophene having 5~22 carbon atoms, or a halogenated derivative thereof, including but not limited to tert-butyl methyl sulfide, tert-butyl sulfide, phenyl sulfide, 4,4'-dichlorophenyl sulfide, 2-methylphenyl sulfide, 2,4,6-trimethyl phenyl sulfide, 4,4'-thio bis(6-tert-butyl-3-methylphenol), thiazole, 2-ethylthiazole, 2,5-dichlorothiazole, 4-methylthiazole, 2-tert-butylthiazole, isothiazole, 4,5-dimethylisothiazole, 5-chloroisothiazole, 2,4,5-tri-tert-butyl isothiazole, thiophene, 2-methylthiophene, 2,5-dimethylthiophene, 3-chlorothiophene, 3,4-dichlorothiophene, 2,3,4-trichlorothiophene, wherein preferably tert-butyl sulfide, 2,4,6-trimethyl phenyl sulfide, 4,4'-thiobis(6-tert-butyl-3-methylphenol), 2-ethylthiazole, 2,5-dichlorothiazole, 2,4,5-tri-tert-butyl isothiazole, 4,5-dimethyl isothiazole, 3,4-dichlorothiophene, 2,3,4-trichlorothiophene, and more preferably tert-butyl sulfide, 4,4'-thiobis(6-tert-butyl-3-methylphenol), 2,4,5-tri-tert-butyl isothiazole, and 2,3,4-trichlorothiophene.

In an embodiment of the present disclosure, the first catalyst and/or the second catalyst may also be present in a supported form, that is, a supported catalyst; a preferred catalyst support is silica gel (the main component is silica), and the catalyst is supported on the catalyst support by impregnation. The loading rates of the first catalyst and the second catalyst are respectively 10%~20% and 5%~15%.

In the present disclosure, in some embodiments using an unsupported catalyst, the catalyst and product are separated by distillation to obtain a chlorophenoxy carboxylic ester; in some embodiment in which the first catalyst and the second catalyst are both supported, the separation of the catalyst from the chlorophenoxy carboxylic ester can be achieved directly by filtration without distillation, particularly, if the first catalyst and the second catalyst are fixed in a reactor, the chlorophenoxy carboxylic ester can be obtained by separation without even filtration, which makes the separation of the catalyst and the product simple and easy, and at the same time improves the use efficiency of the catalyst, saves a lot of energy and is especially suitable for continuous operation.

In embodiments of the present disclosure, the first catalyst is used in an amount of 0.05%~1.0% by weight based on the phenoxycarboxylic ester, preferably 0.25%~1.0%, and more preferably 0.5%~1.0%. The second catalyst is used in an amount of 0.05%~1.0% by weight based on the phenoxycarboxylic ester, preferably 0.2%~0.8%, and more preferably 0.3%~0.5%. If the first catalyst is a supported form, the active ingredient in the supported catalyst is used in an amount of 0.05%~1.0% by weight based on the phenoxycarboxylic ester, preferably 0.25%~1.0%, more preferably 0.5%~1.0%. Here, the active ingredient in the supported catalyst refers to the first catalyst supported on the carrier, and the amount of the active ingredient of the first catalyst=the amount of the supported first catalyst×the loading ratio. If the second catalyst is a supported form, the active ingredient in the supported catalyst is used in an amount of 0.05%~1.0% by weight based on the phenoxycarboxylic ester, preferably 0.2%~0.8%, more preferably 0.3%~0.5%. Here, the active ingredient in the supported catalyst refers to the second catalyst supported on the carrier, and the amount of the active ingredient of the second catalyst=the amount of the supported second catalyst×the loading ratio.

The chlorinating agent according to the present disclosure is preferably chlorine gas, thionyl chloride or sulfuryl chloride, and more preferably chlorine gas or sulfuryl chloride. The present disclosure performs a selectively chlorination on the benzene ring of the synthesized phenoxycarboxylic ester to obtain a chlorophenoxy carboxylic ester. The temperature of the selective chlorination according to the present disclosure may be −20~100° C., preferably −20~60° C., and more preferably −20~20° C. The chlorophenoxy carboxylic ester of the present disclosure refers to a substance having the following structure:

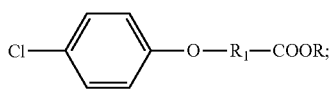

formula III-1

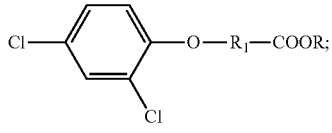

formula III-2

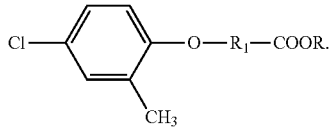

formula III-3

The molar ratio of the phenoxycarboxylic ester to the chlorinating agent of the present disclosure can be selected as follows: if the phenoxycarboxylic ester is of the formula II-1 and the target product is of the formula III-2, the molar ratio of it to the chlorinating agent is 1:(1.98~2.4), preferably 1:(2~2.2), and more preferably 1:(2.02~2.06); if the phenoxycarboxylic ester is of the formula II-1 and the target product is of the formula III-1, the molar ratio of it to the chlorinating agent is 1:(0.99~1.2), preferably 1:(1~1.1), and more preferably 1:(1.01~1.03); and if the phenoxycarboxylic acid is of the formula II-2, the molar ratio of it to the chlorinating agent is 1:(0.99~1.2), preferably 1:(1~1.1), and more preferably 1:(1.01~1.03).

In embodiments of the present disclosure, the phenoxycarboxylic ester is selectively chlorinated to obtain a chlorophenoxy carboxylic ester. Then, the chlorophenoxy carboxylic ester is subjected to an acidolysis reaction to obtain a phenoxycarboxylic acid herbicide represented by formula I. Further, the produced hydrogen chloride can be recovered for an acidolysis reaction of the phenoxycarboxylic ester to directly obtain the phenoxycarboxylic acid and an alcohol.

In embodiments of the present disclosure, a certain amount of acid is added to the chlorocarboxylic ester, and an acidolysis reaction is carried out at a certain temperature for 2 h~4 h, and the alcohol formed in the reaction is distilled off After the reaction is completed, it is cooled to room temperature, filtered, and small amount water is added to wash the filter cake. The filter cake is dried to obtain a phenoxycarboxylic acid herbicide.

The acid of the present disclosure may be hydrochloric acid, phosphoric acid, sulfuric acid or sulfonic acid substances such as sulfonic acid $XSO_3H$, wherein X is an alkyl group, an aryl group, an alkyl or an aryl group substituted by a halogen having 1~18 carbon atoms. In addition, the acidolysis of the present disclosure preferably uses a non-oxidizing, high-boiling, water-soluble phosphoric acid or sulfonic acid as a catalyst to ensure product quality and recycling of the catalyst; compared to the process using solid acid as a catalyst, not only the reaction speed can be accelerated, but also the separation difficulty of the product and the catalyst can be reduced.

In embodiments of the present disclosure, the mass concentration of the acid used for the acidolysis of the chlorophenoxy carboxylic ester may be 5%~35%; and the percentage content of the acid is 0.4~1 times the weight of the chlorophenoxy carboxylic ester. In the present disclosure, the temperature of the acidolysis reaction may be 60~120° C., and preferably 80~100° C. The phenoxycarboxylic acid herbicide obtained by the acidolysis according to the present disclosure has the structure of the formula I, specifically refers to a substance having the following structure:

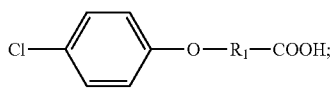

formula I-1

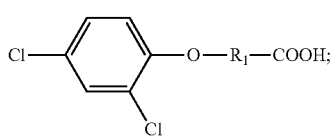

formula I-2

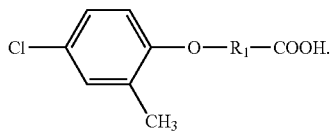

formula I-3

The experiment shows that the content of the phenoxycarboxylic acid herbicide obtained in the embodiment of the present disclosure is ≥98.5%, the total yield is ≥98%, and the washing water and the filtrate are combined and reused. Compared with the conventional art, the method according to the present disclosure effectively avoids the loss of active ingredients and improves the yield of the product. The following are the various target products and impurities (mass content) in some embodiments of the present disclosure:

TABLE 1

Various target products and impurities in some embodiments of the present disclosure

| Target product | Impurities and impurity contents |
|---|---|
| 4-chlorophenoxycarboxylic acid (formula I-1) | 4-chlorophenoxycarboxylic ester (formula III-1) ≤ 0.2% <br> 2,4-dichlorophenoxycarboxylic acid ≤ 0.3% <br> the second catalyst and its chlorinated product ≤ 0.2% |
| 2,4-dichlorophenoxycarboxylic acid (formula I-2) | 2,4-chlorophenoxycarboxylic ester (formula III-2) ≤ 0.2% <br> 4-chlorophenoxycarboxylic acid ≤ 0.2% <br> 2,6-dichlorophenoxycarboxylic acid ≤ 0.1% <br> 2,4,6-trichlorophenoxycarboxylic acid ≤ 0.3% <br> the second catalyst and its chlorinated product ≤ 0.2% |
| 4-chloro-2-methylphenoxycarboxylic acid (formula I-3) | 4-chloro-2-methylphenoxy carboxylic ester (formula III-3) ≤ 0.2% <br> 2-methylphenoxycarboxylic acid ≤ 0.2% <br> 2-chloro-6-methylphenoxycarboxylic acid ≤ 0.4% <br> 2,4-dichloro-6-methylphenoxycarboxylic acid ≤ 0.2% <br> the second catalyst and its chlorinated product ≤ 0.2% |

In summary, the method for preparing the phenoxycarboxylic acid herbicide provided by the present disclosure avoids the production and use of the chlorophenol, and can fundamentally eliminate the formation of highly toxic dioxins, greatly improving product quality and the environment of production sites, while increasing yield. In addition, the present disclosure effectively eliminates the production of high COD and high-salt wastewater by the innovation of the process route, and the output of waste salt (metal chloride) has been reduced by more than 50%, the output of three wastes has been greatly reduced, and the treatment cost of three wastes has dropped significantly, which is conducive to industrialization.

In order to further illustrate the present disclosure, the method for preparing a phenoxycarboxylic acid herbicide according to the present disclosure will be described in detail below with reference to the examples.

In the following examples, the raw materials involved are all commercially available.

Example 1

113.48 g of 99% pure sodium carbonate and 116.20 g of 99% pure methyl chloroacetate were added to 95.06 g of 99% pure anhydrous phenol to react at 90° C. for 2 h. After the reaction was completed, the mixture was cooled to room temperature, filtered and dried, and the dried fraction was collected and combined with a filtrate to obtain 171.66 g of methyl phenoxyacetate with a content of 96.3%.

1.72 g of 99% pure stannic chloride and 0.60 g of 99% pure 2,5-dichlorothiazole were added to the obtained methyl phenoxyacetate, 279.41 g of 99% pure sulfuryl chloride was added at 60° C. to react. After a completion of the addition, the mixture is kept constant in the temperature to react for 0.5 h and the fraction of 115~125° C. was distillated and collected under a pressure of 1 kpa to obtain 234.12 g of methyl 2,4-dichlorophenoxyacetate with a content of 99.18%.

780.40 g of hydrochloric acid with a concentration of 30% was added to the obtained methyl 2,4-dichlorophenoxyacetate, and an acidolysis reaction was carried out at 110° C. for 4 h, and the alcohol formed in the reaction was distilled off. After the reaction was completed, it was cooled to room temperature, filtered, and the filter cake was washed with a small amount of water, and the filter cake was dried to obtain 220.05 g of 2,4-dichlorophenoxyacetic acid. The structure detection spectrum is shown in FIG. 1. FIG. 1 is an $^1$H NMR (DMSO-d6) spectrum; the content was 98.8% and the yield was 98.34% based on phenol.

Comparative Example 1

113.48 g of 99% pure sodium carbonate and 116.20 g of 99% pure methyl chloroacetate were added to 95.06 g of 99% pure anhydrous phenol to react at 90° C. for 2 h. After the reaction was completed, it was cooled to room temperature, filtered and dried, and the dried fraction was collected and combined with a filtrate to obtain 171.66 g of methyl phenoxyacetate with a content of 96.3%.

1.72 g of 99% pure stannic chloride was added to the obtained methyl phenoxyacetate, 279.41 g of 99% pure sulfuryl chloride was added at 60° C. to react. After a completion of the addition, the mixture was kept constant in the temperature to react for 0.5 h and the fraction of 115~125° C. was distillated and collected under a pressure of 1 kpa to obtain 214.33 g of methyl 2,4-dichlorophenoxyacetate with a content of 98.71%.

702.36 g of hydrochloric acid with a concentration of 30% was added to the obtained methyl 2,4-dichlorophenoxyacetate, and an acidolysis reaction was carried out at 110° C. for 4 h, and the alcohol formed in the reaction was distilled off. After the reaction was completed, it was cooled to room temperature, filtered, and the filter cake was washed with a small amount of water, and the filter cake was dried to obtain 200.82 g of 2,4-dichlorophenoxyacetic acid with a content of 98.7% and a total yield of 89.67% based on phenol.

Comparative Example 2

113.48 g of 99% pure sodium carbonate and 116.20 g of 99% pure methyl chloroacetate were added to 95.06 g of 99% pure anhydrous phenol to react at 90° C. for 2 h. After the reaction was completed, it was cooled to the room temperature, filtered and dried, and the dried fraction was collected and combined with the filtrate to obtain 171.66 g of methyl phenoxyacetate with a content of 96.3%.

0.60 g of 99% pure 2,5-dichlorothiazole was added to the obtained methyl phenoxyacetate, 279.41 g of 99% pure sulfuryl chloride was added at 60° C. to react. After a completion of the addition, the mixture was kept constant in the temperature to react for 0.5 h and the fraction of 115~125° C. was distillated and collected under a pressure of 1 kpa to obtain 192.62 g of methyl 2,4-dichlorophenoxyacetate with a content of 98.60%.

780.40 g of hydrochloric acid with a concentration of 30% was added to the obtained methyl 2,4-dichlorophenoxyacetate, and an acidolysis reaction was carried out at 110° C. for 4 h, and the alcohol formed in the reaction was distilled off. After the reaction was completed, it was cooled to room temperature, filtered, and the filter cake was washed with a small amount of water, and the filter cake was dried to obtain 180.71 g of 2,4-dichlorophenoxyacetic acid with a content of 98.5% and a total yield of 80.53% based on phenol.

Comparative Example 3

113.48 g of 99% pure sodium carbonate and 116.20 g of 99% pure methyl chloroacetate were added to 95.06 g of 99% pure anhydrous phenol to react at 90° C. for 2 h. After the reaction was completed, it was cooled to the room temperature, filtered and dried, and the dried fraction was collected and combined with the filtrate to obtain 171.66 g of methyl phenoxyacetate with a content of 96.3%.

279.41 g of 99% pure sulfuryl chloride was added to the obtained methyl phenoxyacetate at 60° C. to react. After a completion of the addition, the mixture was kept constant in the temperature to react for 0.5 h and the fraction of 115~125° C. was distillated and collected under a pressure of 1 kpa to obtain 173.78 g of methyl 2,4-dichlorophenoxyacetate with a content of 98.47%.

568.13 g of hydrochloric acid with a concentration of 30% was added to the obtained methyl 2,4-dichlorophenoxyacetate, and an acidolysis reaction was carried out at 110° C. for 4 h, and the alcohol formed in the reaction was distilled off. After the reaction was completed, it was cooled to room temperature, filtered, and the filter cake was washed with a small amount of water, and the filter cake was dried to obtain 160.82 g of 2,4-dichlorophenoxyacetic acid with a content of 98.3% and a total yield of 71.52% based on phenol.

Example 2

139.61 g of 99% pure potassium carbonate and 152.14 g of 99% pure n-butyl chloroacetate were added to 109.23 g of 99% pure anhydrous o-cresol to react at 120° C. for 4 h. After the reaction was completed, it was cooled to room temperature, filtered and dried, and the dried fraction was collected and combined with the filtrate to obtain 229.80 g of n-butyl o-methylphenoxyacetate with a content of 96.0%.

1.04 g of an iron (III) chloride and 1.50 g of a tert-butyl methyl sulfide were added to the obtained n-butyl o-methylphenoxyacetate, 118.46 g of 99% pure thionyl chloride was added dropwise at 40° C. to react. After a completion of the addition, the mixture was kept constant in the temperature to react for 0.5 h and the fraction of 130~140° C. was distillated and collected under a pressure of 1 kpa to obtain 256.98 g of n-butyl 4-chloro-2-methyphenoxyacetate with a content of 99.01%.

1370.55 g of hydrochloric acid with a concentration of 15% was added to the obtained n-butyl 4-chloro-2-methylphenoxyacetate, and an acidolysis reaction was carried out at 70° C. for 4 h, and the alcohol formed in the reaction was distilled off. After the reaction was completed, it was cooled to room temperature, filtered, and the filter cake was washed with a small amount of water, and the filter cake was dried to obtain 201.33 g of n-butyl 4-chloro-2-methylphenoxyacetate with a content of 98.5% and a total yield of 98.89% based on o-cresol.

Example 3

338.98 g of 99% pure cesium carbonate and 171.30 g of 99% pure n-butyl 2-chloropropionate were added to 95.06 g of 99% pure anhydrous phenol to react at 80° C. for 4 h. After the reaction was completed, it was cooled to room temperature, filtered and dried, and the dried fraction was collected and combined with a filtrate to obtain 229.90 g of n-butyl 2-phenoxypropionate with a content of 96.2%.

1.73 g of 99% pure aluminum oxide and 0.12 g of 99% pure tert-butyl sulfide were added to the obtained n-butyl 2-phenoxypropionate, 76.89 g of 99% pure chlorine gas was introduced at 100° C. to react. After a completion of the addition, the mixture was kept constant in the temperature to react for 0.5 h and the fraction of 130~140° C. was distillated and collected under a pressure of 1 kpa to obtain 257.60 g of n-butyl 2-(4-chlorophenoxy)propionate with a content of 98.77%.

721.28 g of phosphoric acid with a concentration of 25% was added to the obtained n-butyl 2-(4-chlorophenoxy) propionate, and an acidolysis reaction was carried out at 80° C. for 3 h, and the alcohol formed in the reaction was distilled off. After the reaction was completed, it was cooled to room temperature, filtered, and the filter cake was washed with a small amount of water, and the filter cake was dried to obtain 200.46 g of 2-(4-chlorophenoxy)propionic acid with a content of 98.6% and a total yield of 98.56% based on phenol.

Example 4

76.13 g of 99% pure lithium carbonate and 256.37 g of 99% pure n-decyl 2-chloropropionate were added to 95.06 g of 99% pure anhydrous phenol to react at 100° C. for 3 h. After the reaction was completed, it was cooled to room temperature, filtered and dried, and the dried fraction was collected and combined with a filtrate to obtain 318.23 g of n-decyl 2-phenoxypropionate with a content of 95.9%.

15.90 g of a magnesium chloride/silica gel supported catalyst with a loading rate of 20% and 3.18 g of a 2,4,5-tri-tert-butylisothiazole/silica gel supported catalyst with a loading rate of 5% were added to the obtained n-decyl 2-phenoxypropionate, 170.45 g of 99% pure chlorine gas was introduced at 100° C. to react. After a completion of the addition, the mixture was kept constant in the temperature to react for 0.5 h and filtered to obtain 374.49 g of n-decyl 2-(2,4-dichlorophenoxy) propionate with a content of 98.89%.

1497.97 g of trifluoromethanesulfonic acid with a concentration of 10% was added to the obtained n-decyl 2-(2, 4-dichlorophenoxy) propionate, and an acidolysis reaction was carried out at 100° C. for 2 h, and the alcohol formed in the reaction was distilled off. After the reaction was completed, it was cooled to room temperature, filtered, and the filter cake was washed with a small amount of water, and the filter cake was dried to obtain 234.18 g of 2-(2,4-dichlorophenoxy)propanoic acid with a content of 98.8% and a total yield of 98.42% based on phenol.

Example 5

111.34 g of 99% pure sodium carbonate and 217.18 g of 99% pure isooctyl chloroacetate were added to 95.06 g of 99% pure anhydrous phenol to react at 60° C. for 5 h. After the reaction was completed, it was cooled to room temperature, filtered and dried, and the dried fraction was collected and combined with a filtrate to obtain 272.92 g of isooctyl phenoxyacetate with a content of 96.3%.

2.32 g of 99% pure zinc chloride and 1.50 g of 99% pure 4,4'-dichlorophenyl sulfide were added to the obtained isooctyl phenoxyacetate, 136.72 g of 99% pure sulfuryl chloride was added dropwise at 30° C. to react. After a completion of the addition, the mixture was kept constant in the temperature to react for 0.5 h and the fraction of 145~155° C. was distillated and collected under a pressure of 1 kpa to obtain 298.08 g of isooctyl 4-chlorophenoxyacetate with a content of 99.12%.

894.25 g of phosphoric acid with a concentration of 20% was added to the obtained isooctyl 4-chlorophenoxyacetate, and an acidolysis reaction was carried out at 120° C. for 3 h, and the alcohol formed in the reaction was distilled off. After the reaction was completed, it was cooled to room temperature, filtered, and the filter cake was washed with a small amount of water, and the filter cake was dried to obtain 186.29 g of 4-chlorophenoxyacetic acid with a content of 98.9% and a total yield of 98.72% based on phenol.

Example 6

110.27 g of 99% pure sodium carbonate and 156.71 g of 99% pure ethyl 4-chlorobutyrate were added to 109.23 g of 99% pure anhydrous o-cresol to react at 70° C. for 5 h. After the reaction was completed, it was cooled to room temperature, filtered and dried, and the dried fraction was collected and combined with a filtrate to obtain 230.21 g of ethyl o-methylphenoxybutyrate with a content of 96.1%.

0.35 g of 99% pure iron oxide and 1.96 g of 99% pure 2,4,6-trimethyl phenyl sulfide were added to the obtained ethyl o-methylphenoxybutyrate, 78.40 g of 99% pure chlorine gas was introduced at 0° C. to react. After a completion of the addition, the mixture was kept constant in the temperature to react for 0.5 h and the fraction of 130~140° C. was distillated and collected under a pressure of 1 kpa to obtain 255.82 g of ethyl 4-chloro-2-methylphenoxybutyrate with a content of 99.29%.

Figure 2:
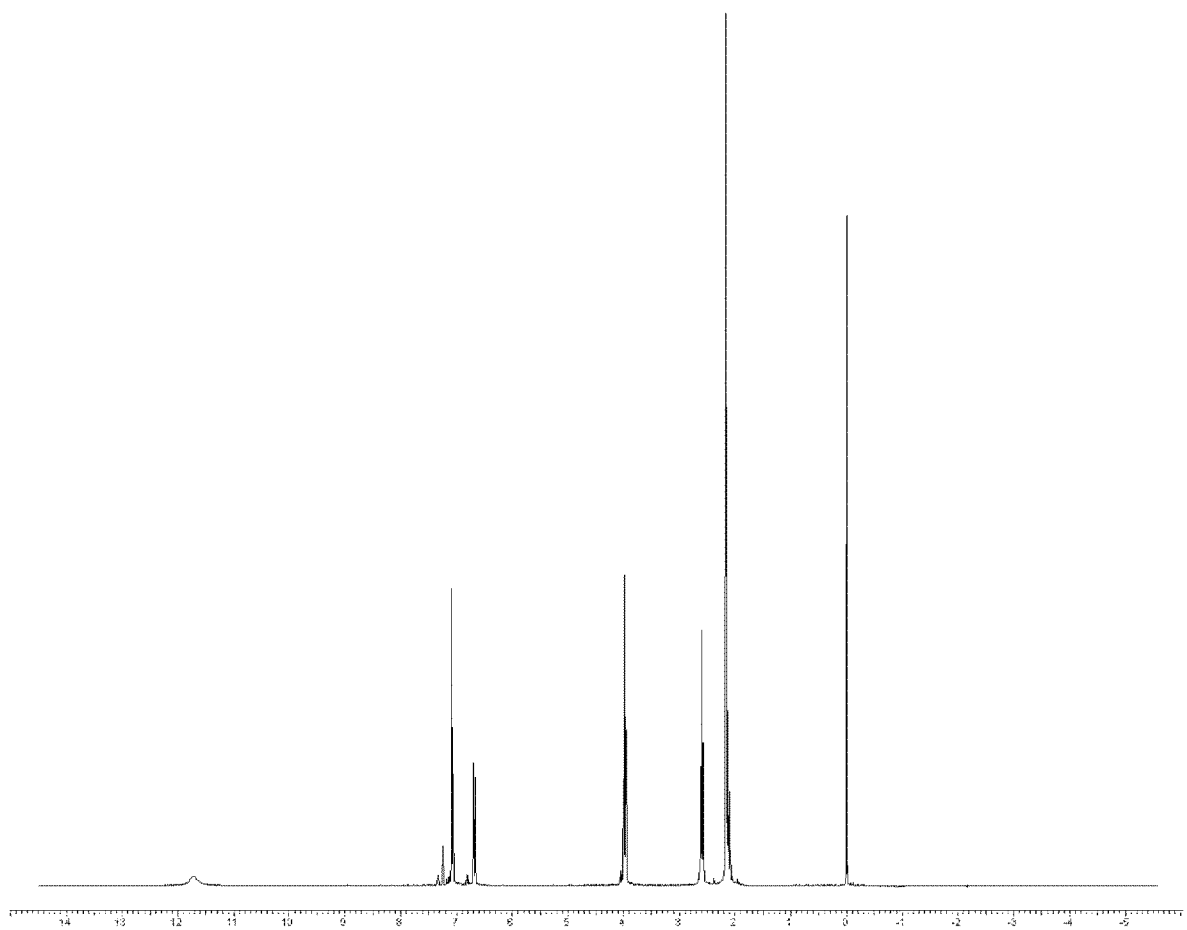
FIG. 2 is a nuclear magnetic resonance spectrum of 4-chloro-2-methylphenoxybutyric acid obtained in Example 6 of the present disclosure.

2046.53 g of octadecylsulfonic acid with a concentration of 5% was added to the obtained ethyl 4-chloro-2-methylphenoxybutyrate, and an acidolysis reaction was carried out at 85° C. for 2 h, and the alcohol formed in the reaction was distilled off. After the reaction was completed, it was cooled to room temperature, filtered, and the filter cake was washed with a small amount of water, and the filter cake was dried to obtain 228.45 g of 4-chloro-2-methylphenoxybutyric acid (MCPB). The structure detection spectrum is shown in FIG. 2. FIG. 2 is a H NMR (CDCl$_3$) spectrum; the content was 98.7%, and the yield was 98.61% based on o-cresol.

Example 7

111.34 g of 99% pure sodium carbonate and 246.66 g of 99% pure isooctyl 4-chlorobutyrate were added to 109.23 g of 99% pure anhydrous o-cresol to react at 90° C. for 2 h. After the reaction was completed, it was cooled to room temperature, filtered and dried, and the dried fraction was collected and combined with a filtrate to obtain 318.59 g of isooctyl o-methylphenoxybutyrate with a content of 95.9%.

1.75 of 99% pure titanium dioxide and 0.80 g of 99% pure 2-ethylthiazole were added to the obtained isooctyl o-methylphenoxybutyrate, 85.67 g of 99% pure chlorine gas was introduced at 50° C. to react. After a completion of the addition, the mixture was kept constant in the temperature to react for 0.5 h and the fraction of 160~170° C. was distillated and collected under a pressure of 1 kpa to obtain 340.17 g of isooctyl 4-chloro-2-methylphenoxybutyrate with a content of 99.08%.

680.33 g of phosphoric acid with a concentration of 35% was added to the obtained isooctyl 4-chloro-2-methylphenoxybutyrate, and an acidolysis reaction was carried out at 95° C. for 3 h, and the alcohol formed in the reaction was distilled off. After the reaction was completed, it was cooled to room temperature, filtered, and the filter cake was washed with a small amount of water, and the filter cake was dried to obtain 228.28 g of 4-chloro-2-methylphenoxybutyric acid with a content of 98.5% and a total yield of 98.30% based on o-cresol.

Example 8

150.77 g of 99% pure potassium carbonate and 118.40 g of 99% pure methyl chloroacetate were added to 95.06 g of 99% pure anhydrous phenol to react at 80° C. for 2 h. After the reaction was completed, it was cooled to room temperature, filtered and dried, and the dried fraction was collected and combined with a filtrate to obtain 172.32 g of methyl phenoxyacetate with a content of 95.8%.

0.09 g of 99% pure lead acetate and 1.29 g of 99% pure 2,3,4-trichlorothiophene were added to the obtained methyl phenoxyacetate, 118.34 g of 99% pure thionyl chloride was added dropwise at 20° C. to react. After a completion of the addition, the mixture was kept constant in the temperature to react for 0.5 h and the fraction of 110~120° C. was distillated and collected under a pressure of 1 kpa to obtain 200.87 g of methyl 4-chlorophenoxyacetate with a content of 98.84%.

401.74 g of sulfuric acid with a concentration of 25% was added to the obtained methyl 4-chlorophenoxyacetate, and an acidolysis reaction was carried out at 80° C. for 2 h, and the alcohol formed in the reaction was distilled off. After the reaction was completed, it was cooled to room temperature, filtered, and the filter cake was washed with a small amount of water, and the filter cake was dried to obtain 186.28 g of 4-chlorophenoxyacetic acid with a content of 98.6% and a total yield of 98.71% based on phenol.

Example 9

1396.1 g of 99% pure potassium carbonate and 1379.7 g of 99% pure isopropyl chloroacetate were added to 950.6 g of 99% pure anhydrous phenol to react at 110° C. for 2 h. After the reaction was completed, it was cooled to room temperature, filtered and dried, and the dried fraction was collected and combined with a filtrate to obtain 2002.3 g of isopropyl phenoxyacetate with a content of 96.2%.

273.29 g of 99% pure sulfuryl chloride wad added dropwise to the obtained isopropyl phenoxyacetate at 70° C. to react. After a completion of the addition, the mixture was kept constant in the temperature to react for 0.5 h and filtered to obtain 261.91 g of isopropyl 2,4-dichlorophenoxyacetate with a content of 98.94%.

3.3 g of a titanium tetrachloride/silica gel supported catalyst with a loading rate of 10% and 44.4 g of a 3,4-dichlorothiophene/silica gel supported catalyst with a loading rate of 15% were respectively added to a three-stage series continuous reactor (100 mL of each volume), and 40.0 g of the isopropyl phenoxyacetate obtained by distillation was added to the first-stage reactor and stirred, and then 54.6 g of 99% sulfuryl chloride was added at 40° C. at a constant rate. After the addition of sulfuryl chloride, 1962.3 g of the isopropyl phenoxyacetate obtained by distillation and 2678.3 g of 99% sulfuryl chloride were added proportionally at a constant rate. With the addition of material in the first-stage reactor, the material overflowed into the second-stage reactor and third-stage reactor. When the second-stage reactor and third-stage reactor also had materials, the temperature was maintained at 40° C., and the reaction materials finally overflowed out of the system from the third-stage reactor to obtain isopropyl 2,4-dichlorophenoxyacetate, while the supported catalyst did not flow out of the system with the material due to its high density. After all the materials had been added, the temperature was kept constant for 30 min, the materials in the first, second and third-stage reactors were filtrated and combined with the isopropyl 2,4-dichlorophenoxyacetate overflowing from the third-stage reactor to obtain 2619.1 g of isopropyl 2,4-dichlorophenoxyacetate with a content of 98.94%

20952.6 g of hydrochloric acid with a concentration of 10% was added to the obtained isopropyl 2,4-dichlorophenoxyacetate, and an acidolysis reaction was carried out at 60° C. for 4 h, and the alcohol formed in the reaction was distilled off. After the reaction was completed, it was cooled to room temperature, filtered, and the filter cake was washed with a small amount of water, and the filter cake was dried to obtain 2200.7 g of 2,4-dichlorophenoxyacetic acid with a content of 98.8% and a total yield of 98.39% based on phenol.

Example 10

109.20 g of 99% pure sodium carbonate and 155.18 g of 99% pure isobutyl chloroacetate were added to 109.23 g of 99% pure anhydrous o-cresol to react at 100° C. for 4 h. After the reaction was completed, it was cooled to room temperature, filtered and dried, and the dried fraction was collected and combined with a filtrate to obtain 229.67 g of isobutyl o-methylphenoxyacetate with a content of 96.1%.

0.57 g of 99% pure aluminum chloride and 1.03 g of 99% pure 4,4'-thiobis(6-tert-butyl-3-methylphenol) were added to the obtained isobutyl o-methylphenoxyacetate, 139.49 g of 99% sulfuryl chloride was added dropwise at 80° C. to react. After the completion of the addition, the mixture was kept constant in the temperature to react for 0.5 h and the fraction of 130~140° C. was distillated and collected under a pressure of 1 kpa to obtain 255.69 g of isobutyl 4-chloro-2-methylphenoxyacetate with a content of 99.09%.

1150.59 g of hydrochloric acid with a concentration of 20% was added to the obtained isobutyl 4-chloro-2-methylphenoxyacetate, and an acidolysis reaction was carried out at 90° C. for 4 h, and the alcohol formed in the reaction was distilled off. After the reaction was completed, it was cooled to room temperature, filtered, and the filter cake was washed with a small amount of water, and the filter cake was dried to obtain 199.21 g of 4-chloro-2-methylphenoxyacetic acid with a content of 99.0% and a total yield of 98.29% based on o-cresol.

Example 11

1396.1 g of 99% pure potassium carbonate and 1521.4 g of 99% pure n-butyl chloroacetate were added to 1092.3 g of 99% pure anhydrous o-cresol to react at 120° C. for 4 h. After the reaction was completed, it was cooled to room temperature, filtered and dried, and the dried fraction was collected and combined with a filtrate to obtain 2298.0 g of n-butyl o-methylphenoxyacetate with a content of 96.0%.

26.8 g of a zinc chloride/silica gel supported catalyst with a loading rate of 15% and 40.2 g of a 3,4-dichlorothiophene/silica gel supported catalyst with a loading rate of 10% were respectively added to a three-stage series continuous reactor (100 mL of each volume), and 20.0 g of the obtained n-butyl o-methylphenoxyacetate was added to the first-stage reactor and stirred, and then 10.3 g of 99% thionyl chloride was added at −20° C. at a constant rate. After the addition of thionyl chloride, 2278.0 g of the obtained n-butyl o-methylphenoxyacetate and 1174.3 g of 99% thionyl chloride were added proportionally at a constant rate. With the addition of material in the first-stage reactor, the material overflowed into the second-stage reactor and third-stage reactor. When the second-stage reactor and third-stage reactor also had materials, the temperature was maintained at −20° C., and the reaction materials finally overflowed out of the system from the third-stage reactor to obtain n-butyl 4-chloro-2-methylphenoxyacetate, while the supported catalyst did not flow out of the system with the material due to its high density. After all the materials had been added, the temperature was kept constant for 30 min, the materials in the first, second and third-stage reactors were filtrated and combined with the n-butyl 4-chloro-2-methylphenoxyacetate overflowing from the third-stage reactor to obtain 2564.1 g of n-butyl 4-chloro-2-methylphenoxyacetate with a content of 99.13%.

13705.5 g of hydrochloric acid with a concentration of 15% was added to the obtained n-butyl 4-chloro-2-methylphenoxyacetate, and an acidolysis reaction was carried out at 70° C. for 4 h, and the alcohol formed in the reaction was distilled off. After the reaction was completed, it was cooled to room temperature, filtered, and the filter cake was washed with a small amount of water, and the filter cake was dried to obtain 2013.1 g of 4-chloro-2-methylphenoxyacetic acid with a content of 98.6% and a total yield of 98.98% based on o-cresol.

It can be seen from the above examples that the content of the phenoxycarboxylic acid herbicide product obtained in the examples according to the present disclosure is ≥98.5%, the total yield is ≥98%, and the washing water and the filtrate are combined and reused.

Some target products and impurities in the examples of the present disclosure are as follows:

TABLE 2

Some target products and impurities in the examples of the present disclosure

| Example | Target product | Impurities and contents |
|---|---|---|
| 2 | 4-chloro-2-methylphenoxyacetic acid | n-butyl 4-chloro-2-methylphenoxyacetate 0.08%, 2-methylphenoxyacetic acid 0.17%, 2-chloro-6-methylphenoxyacetic acid 0.24%, 2,4-dichloro-6-methylphenoxyacetic acid 0.16%, tert-butyl methyl sulfide 0.19% |
| 8 | 4-chlorophenoxyacetic acid | methyl 4-chlorophenoxyacetate 0.03%, 2,4-dichlorophenoxyacetic acid 0.22%, 2,3,4-trichlorothiophene 0.12% |

The present disclosure performs a condensation reaction of phenolic compound to synthesize phenoxycarboxylic ester, and then performs a selective chlorination to synthesize chlorophenoxy carboxylic ester, and finally acidifies to synthesize phenoxycarboxylic acid herbicide. The present disclosure effectively avoids the production and use of chlorophenol with unpleasant odor, fundamentally eliminates the production of highly toxic dioxins, and greatly improves product quality and operating environment at the production site. Moreover, the present disclosure effectively eliminates the production of high COD and high-salt wastewater, and the output of waste salt (metal chloride) has been reduced by more than 50%, which greatly reduces the treatment amount of the three wastes, the difficulty of treating the three wastes, and the treatment cost.

The above description are only preferred embodiments according to the present disclosure, and it should be noted that those skilled in the art can also make several improvements and modifications without departing from the principles of the present disclosure. Such improvements and modifications should also be considered as the scope of the protection of the present disclosure.

What is claimed is:

1. A method for preparing a phenoxycarboxylic acid herbicide, comprising the following steps of:
   S1, mixing an anhydrous phenolic compound, an alkaline substance and a chlorocarboxylic ester, and performing a one-pot condensation reaction in a non-aqueous system to obtain a phenoxycarboxylic ester; the anhydrous phenolic compound is anhydrous phenol or anhydrous o-cresol;
   the general formula of the chlorocarboxylic ester is $ClR_1COOR$, wherein $R_1$ is selected from an alkylene or an alkylidene group with 1~3 carbon atoms, R is selected from an alkyl group with 1~10 carbon atoms or a cycloalkyl group with 3~10 carbon atoms;
   S2, performing a selective chlorination of the phenoxycarboxylic ester with a chlorinating agent in the presence of a first catalyst and a second catalyst to obtain a chlorophenoxy carboxylic ester; the first catalyst is selected from a Lewis acid, and the second catalyst is selected from a thioether compound with 5~22 carbon atoms, a thiazole compound with 5~22 carbon atoms, an isothizaole compound with 5~22 carbon atoms, or a thiophene compound with 5~22 carbon atoms;
   S3, performing an acidolysis reaction of the chlorophenoxy carboxylic ester to obtain the phenoxycarboxylic acid herbicide represented by formula I;

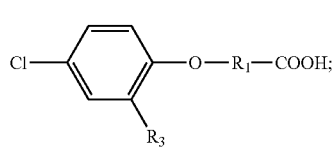

formula I in formula I, $R_1$ is selected from an alkylene or an alkylidene group with 1~3 carbon atoms, and $R_3$ is H, Cl or $CH_3$.

2. The method according to claim 1, wherein in step S1, the alkaline substance is lithium carbonate, sodium carbonate, potassium carbonate or cesium carbonate.

3. The method according to claim 2, wherein in step S1, the molar ratio of the anhydrous phenolic compound to the alkaline substance is 1:(1~1.08), and the molar ratio of the anhydrous phenolic compound to the chlorocarboxylic ester is 1:(1~1.08).

4. The method according to claim 1, wherein in step S1, the temperature of the condensation reaction is 60~120° C.

5. The method according to claim 1, wherein the step S1 comprising: mixing the anhydrous phenolic compound, the alkaline substance and the chlorocarboxylic ester, then heating the mixture and keeping the temperature constant to react for 2 h~5 h to obtain a liquid containing condensation product, and filtering and drying to obtain a phenoxycarboxylic ester.

6. The method according to claim 1, wherein in step S2, the chlorinating agent is chlorine gas, thionyl chloride or sulfuryl chloride.

7. The method according to claim 6, wherein in step S2, the molar ratio of the phenoxycarboxylic ester to the chlorinating agent is 1:(1.98~2.4), and in step S3 $R_3$ is Cl;
   or alternatively, the molar ratio of the phenoxycarboxylic ester to the chlorinating agent is 1:(0.99~1.2), and in step S3 $R_3$ is H or $CH_3$.

8. The method according to claim 1, wherein in step S2, the first catalyst is used in an amount of 0.05%~1.0% by weight based on the phenoxycarboxylic ester, and the second catalyst is used in an amount of 0.05%~1.0% by weight based on the phenoxycarboxylic ester.

9. The method according to claim 6, wherein in step S2, the temperature of the selective chlorination is −20~100° C.

10. The method according to claim 1, wherein in step S3, the acid used for the acidolysis is hydrochloric acid, phosphoric acid, sulfuric acid or sulfonic acid.

* * * * *